United States Patent [19]

Durst et al.

[11] Patent Number: 5,271,903
[45] Date of Patent: Dec. 21, 1993

[54] SUPERCRITICAL FLUID EXTRACTION RESTRICTOR AND COLLECTION SYSTEM

[75] Inventors: Kevin Durst, Salt Lake City; Nathan L. Porter, Kaysville; Ross A. Riches, Sandy; Gary L. Gleavae, West Valley; R. Brent Nielsen, Salt Lake City; Bruce E. Richter, Sandy, all of Utah

[73] Assignee: Dionex Corporation, Sunnyvale, Calif.

[21] Appl. No.: 591,612

[22] Filed: Oct. 2, 1990

[51] Int. Cl.⁵ .................. B01L 11/00; B01D 11/00
[52] U.S. Cl. ........................... 422/101; 422/81; 210/511; 73/864.15; 73/864.86; 73/864.91
[58] Field of Search ............ 422/100, 102, 103, 104, 422/81, 101; 73/864.15, 864.59, 864.86, 864.87, 864.91; 436/54; 210/634, 511

[56] References Cited

U.S. PATENT DOCUMENTS 4,962,275  10/1990  Bruno .................. 210/634
5,087,360   2/1992  Wright et al. ......... 210/634 X

OTHER PUBLICATIONS

Wright (Anal. Chem. 59, pp. 38–44, 1987).
Hawthorne (Anal. Chem., vol. 60, No. 5, pp. 472–477) 1988.
Hawthorne (Anal. Chem., vol. 59, p. 1705, 1987).
Onuska (Journal of High Resolution Chromatography, vol. 12, p. 357, Jun. 1989).
Schneiderman, et al. (J. or Chromatography, vol. 409, pp. 343–353, 1987).
Schneiderman et al. (J. Chrom. Sci., vol. 26 p. 458, Sep. 1988).
Hawthorne and Miller (J. of Chrom. Science, vol. 24, p. 258 Jun., 1986).
Stahl (J. of Chromatography, vol. 142, pp. 15–21, 1977).

Primary Examiner—James C. Housel
Assistant Examiner—Maureen M. Wallenhorst
Attorney, Agent, or Firm—Flehr, Hohbach, Test, Albritton & Herbert

[57] ABSTRACT

An apparatus for receiving chemical compounds carried in a high pressure effluent fluid stream from supercritical fluid extraction. The apparatus includes a heated conduit connected to supercritical fluid extraction device through which an effluent stream flows. The exit port of the heated conduit is located within the airspace of a decompression zone which is free of liquid. A liquid solvent chamber is provided in open communication with the downstream end of the decompression zone into which the effluent stream flows for the recovery of chemical compounds therein.

14 Claims, 7 Drawing Sheets

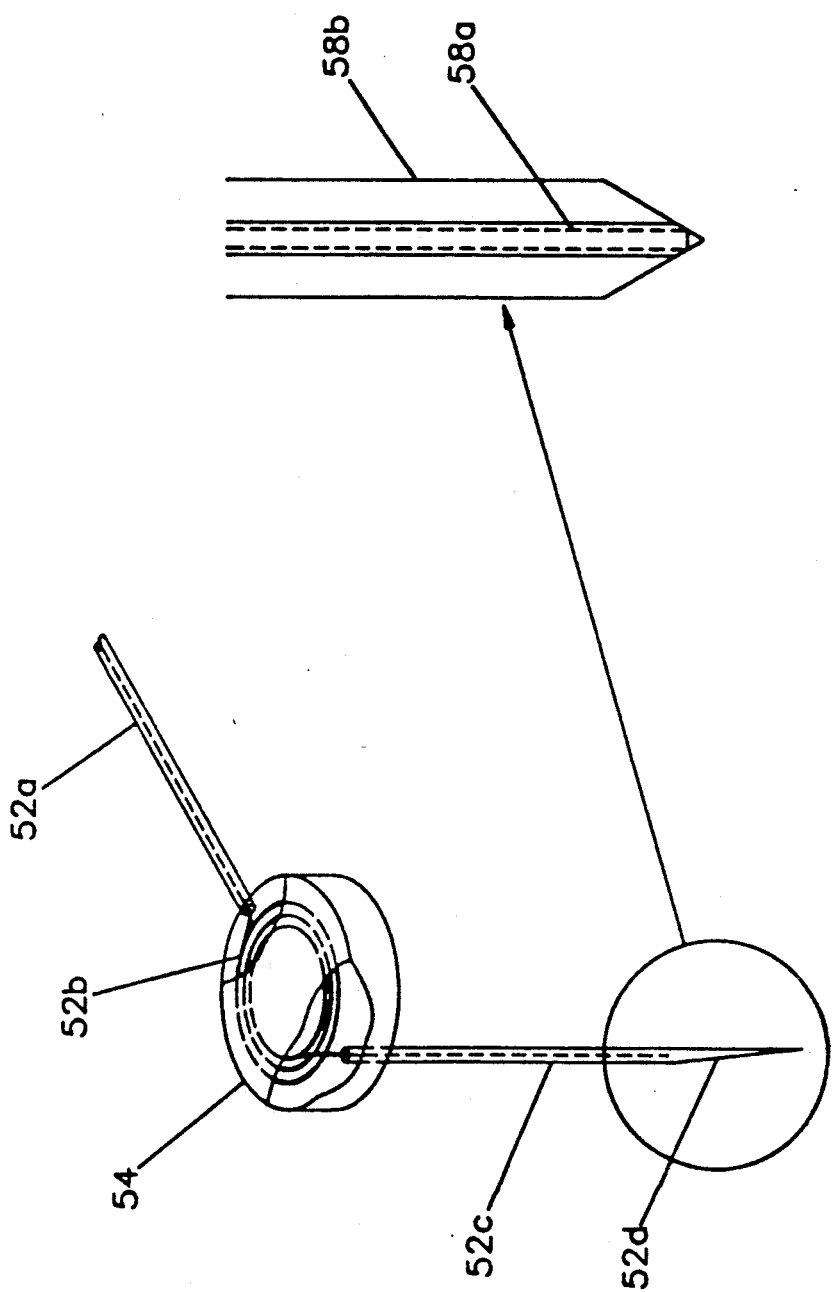

SUPERCRITICAL FLUID EXTRACTION RESTRICTOR AND COLLECTION SYSTEM

BACKGROUND OF THE INVENTION

This invention relates to the collection for analysis or other purpose of chemical compounds extracted by supercritical fluid from samples of interest. Such extraction is known as supercritical fluid extraction (SFE).

Extraction of chemical compounds or elements from complex mixtures of chemical compounds or elements is important in many industries and disciplines. Complex extraction techniques and apparatuses have been developed to isolate compounds or elements of interest in pollution samples, soil samples, biological tissue, drugs, oils, metals, and thousands of other substances and matrices. The compounds or elements are extracted from the samples through various techniques, and once isolated, they are collected by some technique and used, further processed, or analyzed.

In SFE, the sample is exposed to a supercritical fluid solvent (typically $CO_2$) under supercritical conditions. A supercritical fluid exists when a material is near or above its critical temperature and pressure (critical point). At pressures and temperatures above the critical point, this single phase has properties which are intermediate between those of the gas and liquid phases and are dependent on the fluid composition, pressure, and temperature. Supercritical fluids are highly compressible just above their critical points. Near the critical point, small changes in pressure result in large changes in density of the fluid. The density of a supercritical fluid is typically about $10^2$ to $10^3$ times greater than that of the gas. Consequently, molecular interactions increase due to shorter intermolecular distances. However, the diffusion coefficients and viscosity of the fluid, although density dependent, remain more similar to that of gas. Supercritical fluids have greatly enhanced solubilizing capabilities compared to the subcritical gas and higher diffusion coefficients, lower viscosity, and an extended temperature range compared to the corresponding liquid. These properties allow similar solvent strengths as liquids but with greatly improved mass-transfer properties which provide the potential for more rapid extraction rates and more efficient extraction due to better penetration of the matrix.

The substance at this point has basically the properties of a liquid and gas simultaneously. Solvents used at supercritical conditions have very effective solvating properties when exposed to a sample. The low viscosities of the supercritical fluids permit better penetration of the sample matrix for better extraction efficiency. The fast diffusion rates in supercritical fluids allow SFE to take place in minutes as compared to hours in liquids. Often the solvent is many times more effective in extracting a compound from a sample at supercritical conditions than at ambient conditions or even ambient pressure and elevated temperatures. Thus, much smaller samples and amounts of solvents can be used to achieve the same concentration of the extracted compound of interest. Compounds which are difficult or impossible to extract from a sample at ambient conditions, or even in a Soxhlet at elevated temperatures, can be routinely extracted using SFE techniques. SFE is performed in cells which contain the sample and allow exposure of the sample to the solvent at supercritical temperatures and pressures.

Additionally smaller amounts of solvent are used in SFE techniques. Many of the commonly used supercritical fluids are gases at room temperature and pressure, and as a result are much easier to dispose of. The environmental hazards to the public and the laboratory worker is substantially reduced and can be nearly eliminated if careful techniques are followed. Smaller amounts of sample can also be used.

Although SFE techniques have numerous advantages over traditional extraction techniques, such as percolation and Soxhlet techniques, several disadvantages have curtailed its use for routine extraction of multiple samples.

Compounds extracted for analytical purposes are analyzed by a variety of methods, including supercritical fluid chromatography, mass spectrometry, infrared spectroscopy, thin layer chromatography, and many other methods. The extracted compound, or solute, must be introduced directly to the analytical apparatus or collected for further processing or indirect introduction to the analytical apparatus.

Interfacing between the SFE apparatus and the analytical apparatus, or even collection of the solute, has proven to be difficult. The SFE process is carried out at high pressures, often on the order of 10,000 pounds per square inch, and the analytical techniques are most often performed at ambient pressure, or even in a vacuum as in the case of mass spectrometry. At best, interfacing an SFE apparatus for direct introduction into an analytical apparatus is difficult, and in some cases, it is nearly impossible to achieve the interface.

"On-line analysis" is an analytical technique where the solute is introduced directly from the extraction process to the analytical apparatus. On-line analysis using SFE and a supercritical fluid chromatographic apparatus (SFC) has become an effective analytical combination. The supercritical fluid chromatograph can readily accept the SFE solute because of mutual compatibility between SFE and SFC.

The SFE-supercritical fluid chromatographic on-line combination is particularly effective for the analysis of heavy, greater than C35, organic compounds.

On-line analysis of lighter weight compounds of interest can be achieved by introducing the solute at supercritical conditions directly into a gas chromatographic column inside of a gas chromatograph.

The compounds of interest are condensed or deposited on the gas chromatographic column or other trapping means and then separated and eluted from the column and detected using standard gas chromatographic techniques. Gas chromatographic techniques cannot generally analyze heavy, organic compounds because of low volatility.

If the solute eluting from the SFE apparatus is collected for other types of analysis, additional preparation, or use; the solute at supercritical conditions must be brought to ambient pressure and temperatures. Achieving such a reduction in pressure and temperature and effectively collecting the compounds of interest is difficult. This is generally called off-line SFE.

In order to maintain supercritical pressure in the SFE apparatus, the pressure must be reduced slowly at the outlet of the apparatus. The outlet cannot simply be open to the atmosphere. It must be restricted to allow gradual depressurization of the solute. Numerous methods have been used to restrict the pressure drop.

In order to maintain supercritical pressures within the SFE system, any port which allows supercritical fluid to be depressurized and exit the system must act to restrict the exit process. The restriction has to be sufficient to allow the pressure pumps to maintain the supercritical pressure within the SFE system. As the supercritical fluid or solvent passes through the restricted area from the supercritical pressure to a lower pressure, its ability to carry its solutes is reduced and the solutes are deposited at the port. The port can be a small orifice, nozzle, tube, valve, or any other system which allows the fluid to pass through the port in a restricted manner.

The deposition of solutes at the port is one of the major problems encountered in off-line SFE techniques. The solutes are deposited and clog the port. The invention overcomes such problems.

Various techniques have been used to restrict the depressurization of the supercritical solutes to lower pressure where they can be collected or analyzed after off-line SFE.

Wright (Anal. Chem. 59, pp. 38-44, 1987) describes a technique where a stainless steel capillary column is crimped on its exit end in order to form a restriction. This technique has many disadvantages, even though it is commonly used. For example, the stainless steel surface actually forms a catalytic surface which causes decomposition of analytes when heated. Stainless steel tubing is difficult to make and obtain in very small internal diameters. Fifty microns is about the smallest internal diameter stainless steel tubing available. Restriction devices usually require a port with a smaller opening than 50 microns. Thus, the stainless steel tube is crimped at the exit end.

Crimping the tube presents two major problems. First, the crimp cannot be effectively formed in the same manner each time. Therefore, reproducibility of conditions is impossible. Because SFE analytical extractions can use very small volumes, which is advantageous in many cases, small inconsistencies in apparatus conditions can have a large effect on the analysis results. Second, the crimp is required to restrict supercritical fluid within the SFE apparatus as it exits to a lower pressure. The high pressure maintained within the SFE system pushes the crimp open, thus reducing the crimp's effectiveness and varying conditions even within the same extraction.

A changing flow rate during the extraction will make calculation of the total volume of solvent flow difficult or impossible, and conditions of the extraction cannot be reproduced. Samples cannot be compared because they were not obtained under the same extraction conditions. A small change in the opening size of the crimp can make a significant change in the total volume of solvent passing through the system.

Crimping tubes in order to restrict exit of the solute from an SFE system makes meaningful direct quantitative comparison of results from the simultaneous extraction of multiple samples within the same SFE apparatus impossible.

The stainless steel tubing must be heated, as must any other tube acting as a restrictor, to prevent deposition of solute compounds in the tube as the supercritical fluid falls below the supercritical temperature and pressure. Commonly, this heating is achieved by having the tube within the oven, as in the case of on-line analysis procedures using supercritical fluid extraction. The tube is also commonly wrapped with a heat tape of some type which either insulates the tube or actually has a heating capacity and heats the tube to maintain the needed temperature to prevent deposition of solute compounds in the tube. Wright describes a technique of applying an electric current to the stainless steel tube which is crimped. The electric heating technique obviously only works when electrically conductive materials are used to form the restriction tube.

In each case described, heating of the restriction area or tube is not isothermal. It is important that the temperature along the tube, or within the area, be isothermal. If the temperature is variable, compounds being carried in the tube will precipitate where the temperature is below that required to retain such compound or compounds in the dissolved state in the solvent. The diversity of the supercritical fluid actually changes resulting in the precipitation. This deposition clogs the tube and results in erroneous extraction analysis because not all of the samples of interest are eluted from the extraction system.

Very small diameter orifices, usually laser drilled in plates made of metal, sapphire, or other substances, have proven to be ineffective as restrictors. Sputtering occurs when the orifice starts to clog and sample is lost, the plates are hard to attach to the SFE apparatus and cooling is a problem at the exit of the orifice. Clogging is common at the orifice.

Ovens such as gas chromatography or supercritical fluid ovens are specifically designed to maintain a column or tube at an isothermal temperature. In on-line analyses, the restrictor tube can be within such an oven. This is expensive because the oven must be dedicated to use in the SFE process.

Another technique for restriction is use of a fused silica tube. The fused silica tube can be readily obtained with small inside diameters, i.e., 10-50 microns. If the tube has a small enough inside diameter, 10-30 microns, and has a uniform diameter along its length, a linear restriction of the pressure inside the SFE system results along the tube. Pressure is progressively lost, in a direct relationship to the length of the tube, as the solute moves through the tube.

In the on-line system, the SFE system is coupled directly to the chromatographic analysis system. One sample is prepared or extracted and analyzed. Thus, the analytical system is dedicated to the SFE system.

In off-line extraction techniques, numerous extractions can take place simultaneously and several chromatographic systems can be utilized simultaneously. Productivity is greatly improved using an off line system, and the expense of analysis is also greatly decreased.

On-line SFE techniques are reported to be most suitable to gas chromatographic (GC) techniques because the GC techniques analyze the lighter organics or hydrocarbons and with samples of light weight hydrocarbons, the restrictors are not clogged or plugged as easily because light weight hydrocarbons are not as readily precipitated from the solvent. Analysis of heavy weight hydrocarbons obtained from SFE extractors is much more difficult because of the problems with restrictor clogging.

Hawthorne (Anal. Chem., Vol. 60, No. 5, p. 474, Mar. 1, 1988) reports the use of fused silica capillary tubing as a restrictor in an on-line connection of an SFE apparatus to a gas chromatograph (GC). A stainless steel frit was used prior to the restrictor capillary tubing in order to prevent the sample particles from plugging the outlet of the restrictor. Although the capillary tube was effective in controlling the depressurization of the supercritical solute, a new restrictor had to be used for each extraction. Use of a new restrictor with each extraction proves to be time consuming and expensive if multiple samples are analyzed on a routine basis. The fused silica tube is not the expense, as pointed out by Hawthorne (Anal. Chem., Vol. 59, p. 1706, 1987), the tedious labor is the expense. When multiple extractions are being routinely performed, the work of changing the restrictor with each extraction becomes significant.

Not only has the capillary column been found to become fragile and break with a single use, Onuska (Journal of High Resolution Chromatography, Vol 12, p. 357, June 1989) reports that a new restrictor must be used every second extraction, because a single restrictor, if used for several extractions, yields lower recoveries of the compounds of interest due to changes in hydrodynamic profile caused by deposition of material in the restriction tube. The tube is eventually plugged in such cases. In the present invention, the tube does not readily plug and the recovery of the analytes or solutes remains constant, at or near 100%, even after many uses of the same restriction tube.

When analytes are deposited in the restriction tube, successive extraction effluents can become contaminated from deposits made during prior extractions. Thus, a new restriction tube is used in many cases.

Schneiderman, et al. (J. of Chromatography, Vol. 409, pp. 343-353, 1987), have used an off-line SFE process to collect a median weight hydrocarbon for analysis. They have used a valve to restrict the depressurization of the supercritical fluid solute, and the solute or extract was collected on a silica gel trap. The trap was then washed with methylene chloride/acetone (50:50), the solution was evaporated to dryness and the residue was reconstituted in 10 ml of a solvent before analysis. This represents one technique used in state-of-the-art SFE off-line extractions.

Stahl (J. of Chromatography, Vol. 142, pp. 15-21, 1977) has also demonstrated the use of a valve used as a restrictor and has used a thin layer chromatography plate as a trapping mechanism and analyzer. The use of a valve for restriction is a very expensive form of restrictor. A valve does not serve well as a restrictor because it is very difficult to clean. The lubricants used to make the valve function and the residues from past samples or solutes are sources of contamination which are difficult to remove and are very significant in sensitive analytical studies. Additionally, valves are not each made the same and they are difficult to control flow rates with so that the flow rate is reproducible from sample to sample and valve to valve.

Off-line SFE requires some means to trap the compounds or elements of interest that have been dissolved in the supercritical fluid solvent. Schneiderman et al (J. Chrom. Sci., Vol 26, p. 458, Sept. 1988) used a silica gel trap. It is common to use commercially prepared column packing or other adsorbent material such as Tenax TM to trap solutes of interest. The extracted compounds or elements of interest are precipitated in the area of packing when the density of the supercritical fluid solvent changes upon exit from the restrictor. The compounds and elements are chemically trapped by the packing, whatever form it takes. The compounds may be lost if there is a "break through" where the exiting solvent fluid or gas (most supercritical fluid solvents are gases, such as $CO_2$, at ambient temperatures and pressures) passes through the packing carrying the solute and the solute is not exposed to the packing and thus is never trapped on the packing surface. Or, the packing may become saturated, and untrapped solutes can be lost.

Once the analytes or compounds of interest are trapped on the packing surface, they must be removed with some type of a solvent before they can be analyzed or otherwise used. A relatively large amount of solvent must be used and, at least in the case of most analyses, that solvent must be evaporated in order to concentrate the sample and perform a trace analysis. Each step of collection, dissolving, concentration, storage, etc., may result in the loss of some of the compounds of interest, especially light molecular weight hydrocarbons, or contamination of the solute from dirty glassware or solvents. Additionally, each step requires equipment and manpower; thus, making the collection of the compounds of interest more expensive and dangerous.

Use of a packed bed with silica gel, or any other packing, as a trap results in a poor recovery of the compounds of interest. Such poor recovery may be a result of either a failure to trap or secure retention of the compounds of interest on the packing, which does not release the compounds readily when the packing is washed in order to try and bring them back into solutions. Washing the packing, redissolving, and concentrating of the analytes after the SFE process, makes the SFE process much less effective. Its effectiveness is literally diluted and polluted.

Low molecular weight compounds are especially difficult to trap following an SFE process. Two primary techniques have been used to trap such compounds. The depressurizing supercritical fluid solute is bubbled through a solvent or the trapping mechanism is held at a cryogenic temperature. The best recovery of such compounds has been reported at between $-30°$ C. and $-60°$ C. Hawthorne et al (Anal. Chem, Vol. 59, p. 1706, 1987) and Hawthorne and Miller (J. of Chrom. Science, V. 24, p. 258, June, 1986) reports use of the bubbling technique using methylene chloride as the trapping solvent. It is noted that none of the methylene chloride is lost because of the cooling effect caused by the rapid expansion of the supercritical fluid as it exists in the restrictor.

The rapid depressurization of the supercritical fluid at the end of the restrictor has an adiabatic cooling effect which compounds the plugging or clogging of the restrictor. Even though the end of the restrictor may be in a solvent, the cooling effect is so pronounced that plugging is still a problem. Plugging is not as big a problem when only light molecular weight compounds are in the sample, even though a lower flow rate is commonly used to facilitate collection of such compounds. Lower flow rates will almost guarantee plugging of the fused silica or crimped stainless steel tubing restrictors if heavy molecular weight compounds are present in the sample.

SUMMARY OF THE INVENTION

In accordance with the present invention, a method and apparatus are disclosed for recovering chemical compounds carried in a high pressure effluent fluid stream from supercritical fluid extraction. The effluent stream flows through a heated conduit which restricts flow (a capillary tube) to exit a port in a decompression zone free of liquid. The effluent then flows into a liquid solvent zone containing liquid solvent. The low molecular weight compound is trapped in the liquid solvent zone. Where the effluent from supercritical fluid extraction also includes high molecular weight compounds, they are deposited on the walls of the decompression zone and subsequently removed in a liquid solvent.

The above system can be connected to analytical apparatus such as a chromatography column in which a number of chemical compounds in the effluent can be separated followed by detection.

Apparatus for performing the above method includes a decompression chamber connected by a flow restricting conduit (capillary tube) to supercritical fluid extraction means. Means is provided for heating the conduit. A liquid solvent chamber means is provided in open communication with the downstream end of the decompression chamber means.

A preferable capillary conduit (tube) is formed of multi-layered tubing with an inner fused silica tube bonded to an outer heat conductor metal tube and includes a coiled segment imbedded in a heat conductive block. The capillary tube slowly reduces pressure without crimping or other constriction. Preferably, the conduit terminates at its downstream end in an exit port formed to pierce a septum seated across the decompression means inlet port.

BRIEF DESCRIPTION OF THE DRAWINGS

FIG. 4 is detailed view of the restrictor of FIG. 3.

FIG. 5 is an expanded view of the exit end of the restrictor taken along the line 4—4.

DETAILED DESCRIPTION OF THE PREFERRED EMBODIMENTS

Figure 1:
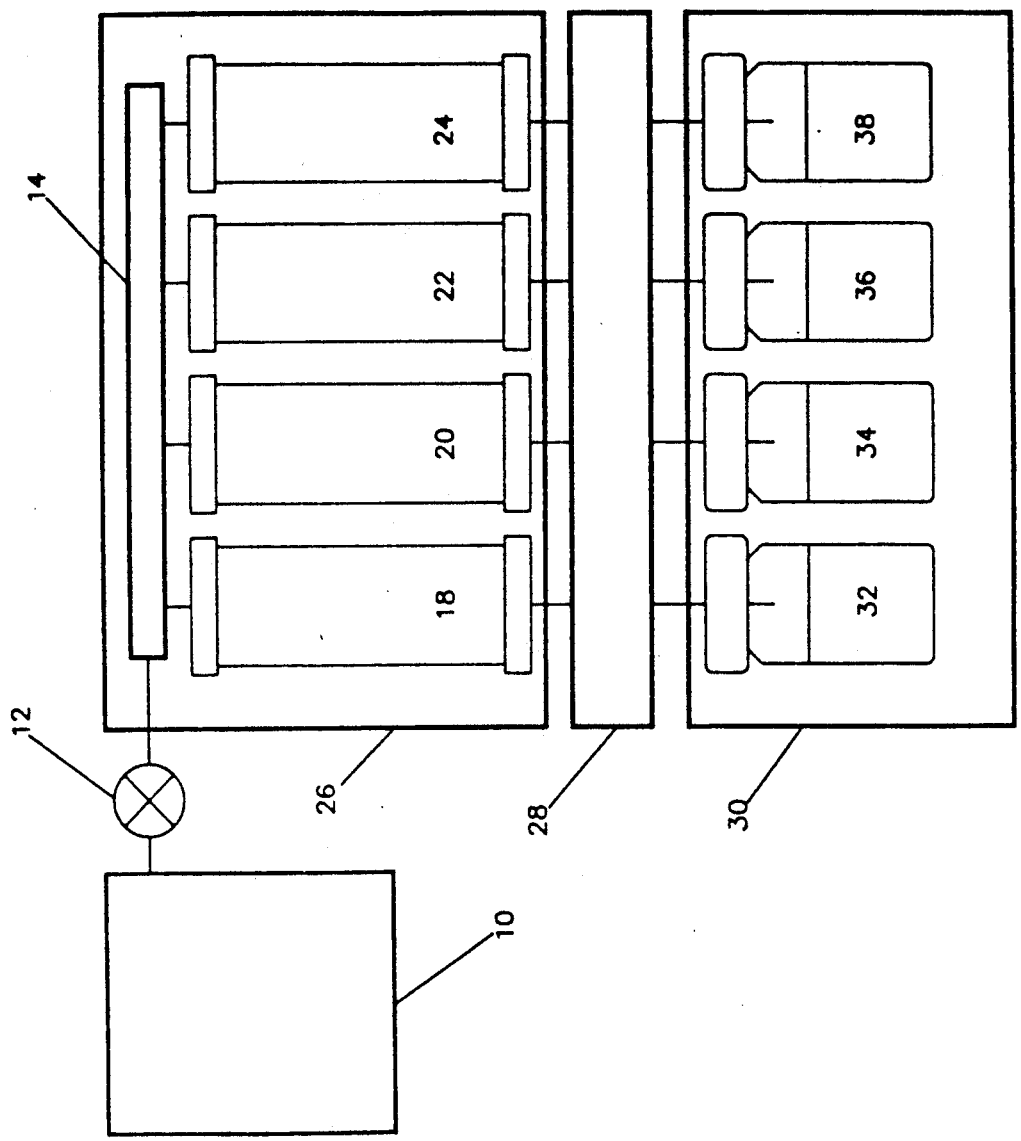
FIG. 1 is a schematic representation of an SFE restrictor and collection system.

Referring to FIG. 1, a conventional SFE pump 10 is connected by valve 12 to a manifold 14 which in turn connects in parallel to a series of conventional supercritical fluid extraction cells 18, 20, 22 and 24, respectively, contained with an oven 26. The pump may be of a syringe or reciprocal design capable of delivering pressurized, liquidified gas at a pressure of at least 6000 psi. A suitable cell is the 6000 PSI Dionex Cell. The oven may be similar to a gas chromatographic oven, heated in a conventional manner, e.g. by an electrical heating element.

The SFE cells are connected by a restrictor conduit through a restriction zone 28 to a trapping or collection region for solute 30 illustrated in the form of vials 32, 34, 36 and 38, respectively.

Figure 2:
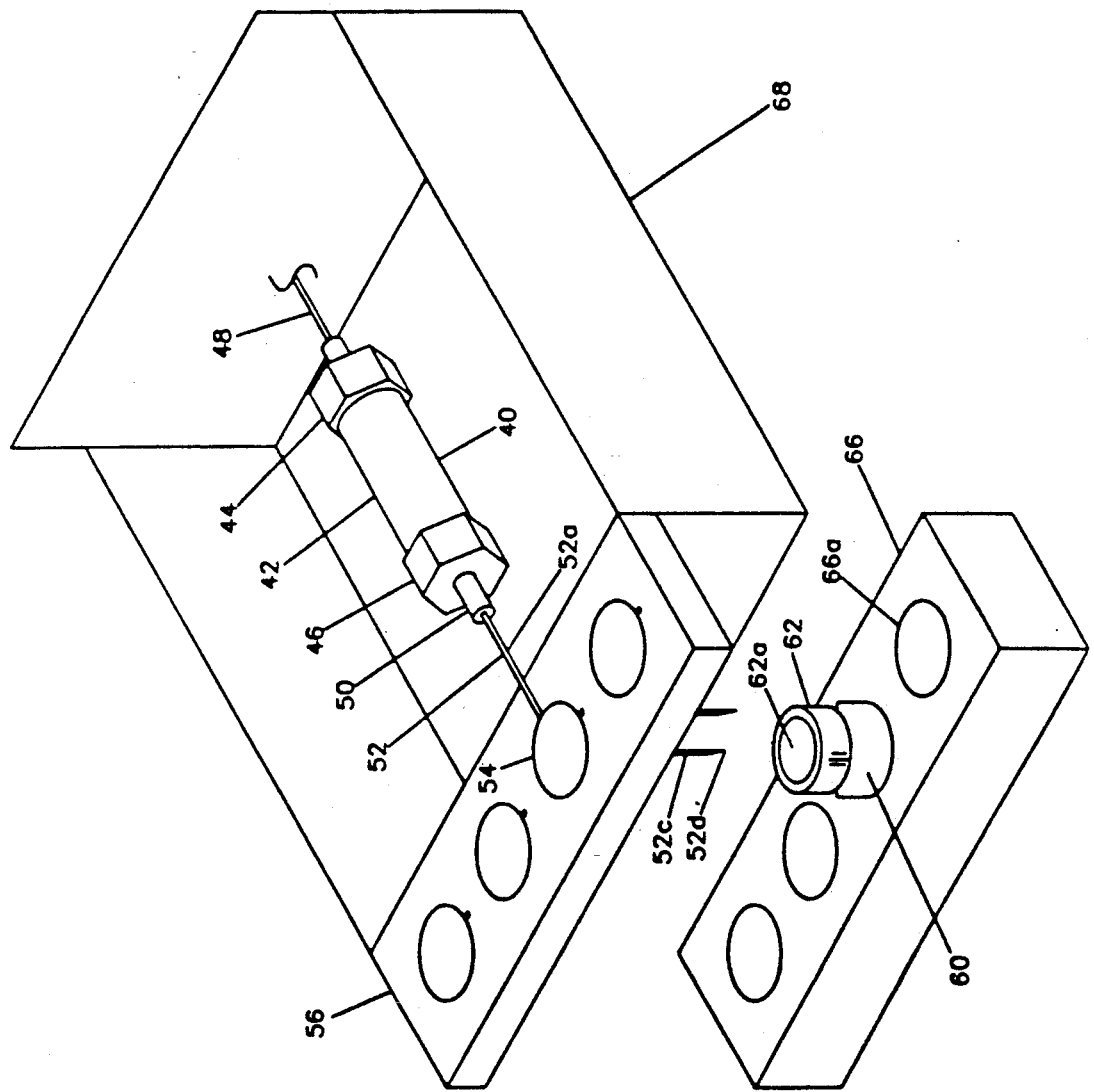
FIG. 2 is a schematic perspective view of the system of FIG. 1.
Figure 3:
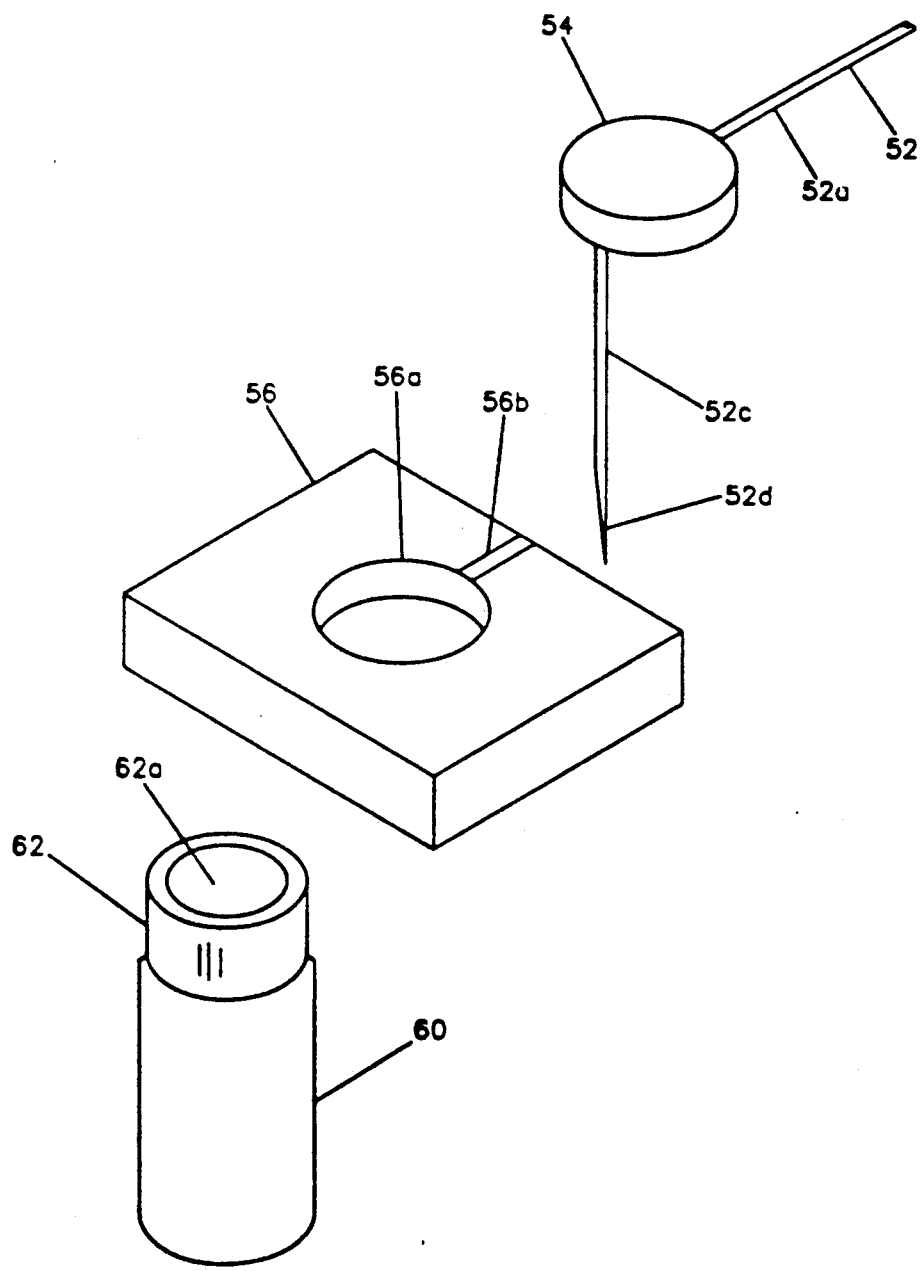
FIG. 3 is an exploded view of the restrictor, heating region and collection vial of the system of FIGS. 1 and 2.

Referring to FIGS. 2-4, more detailed schematic views of the system are illustrated in conjunction with a single SFE sample cell 40 representative of the other sample cells. Such cell includes chamber 42 bounded by inlet and outlet fittings 44 and 46, respectively. Supercritical fluids are pumped via line 48 to fitting 44 from pumping means, not shown, (e.g. a DSTV-122 15k PSI reciprocating pump sold by Haskel, Inc., Burbank, Calif.). Outlet fitting 46 is threadedly connected via internally threaded coupling 50 to a male threaded end of a straight horizontal inlet portion 52a of capillary restrictor conduit 52. Conduit 52 includes a coiled central portion 52b embedded into a restrictor wafer 54 and a downwardly directed outlet portion 52c terminating in a needle 52d or other sharp point suitable for penetrating a septum. Outlet portion 52c is disposed radially inwardly from the wafer cylindrical outer wall to permit needle 52d to penetrate the septum at the desired location.

Wafers 54 are seated spaced in cylindrical wells 56a of a restrictor heating block 56 suitably formed of heat conductive metal such as aluminum. Slots 56b provide channels for restrictor portion 52a to seat wafer 54 on well bottom walls, not shown, of well 56. The bottom wall includes an opening aligned with needle 52d.

As illustrated, the collection vessel is in the form of collection vial 60 which includes a cap 62 with a pierceable septum portion 62a suitably formed of a thin rubber sheet. Vial 60 is removably disposed in well 66a of vial cooling block 66, suitably cooled by flowing refrigeration through piping (not shown) or by the use of thermoelectric chips.

In operation, cooling block 66 is rotatable about 30° from the vertical by a motor connected to a pivotal drive to provide ready access to the vials. Then, block 66 is rotated back to the illustrated vertical position and is pushed by a motor upwardly so that the vial septum 62a is pierced by stationary needle point 52d. This causes restrictor needle 52d to penetrate into the interior of collection vial 60. Oven 68 surrounds and supports SFE cell 42, wafer 54 and restrictor heating block 56. Oven 68 and heating block 56 have independent separate heaters and temperature controls t maintain different temperatures under substantially isothermal conditions. The oven and heating block are thermally insulated from each other.

Referring to FIGS. 4 and 5, the preferred form of restrictor conduit 58a includes a fused silica inner tube 58a bonded to an outer metal tube 58b along its major length and, preferably, its entire length. One mode of construction is to place the fused silica within the metal tubing with a space therebetween which can be filled with heat conductive epoxy resin which solidifies in situ for uniform heat distribution (e.g. epoxy H65-175MP sold by Epotec Technologies, Billercia, Me.).

Coil restrictor segment 52b which is preferably imbedded in a heat conductive material such as Thermalbond 495i sold by Thermalloy, Inc., Dallas, Tex., forming wafer 54. The combination of coil restrictor segment 52b and heat conductive wafer 54 provides excellent heat transfer to maintain isothermal conditions.

As set out above, coupling 50 is threadedly connected to restrictor conduit 52 by exterior metal tubing. This eliminates direct interface between the coupling and internal fused silica which could act as a point of tension to cause the fused silica to become brittle and break. In a preferred embodiment, coupling 50 and tube 52 provide a stainless steel to stainless steel connection. This system permits multiple uses of the restrictor without cracking of the fused silica.

The inner diameter in length of restrictor capillary conduit 52 is adjusted to the desired degree of pressure release from SFE. It is preferably a capillary tube with an internal diameter between about 10 to 100 microns and lengths from about 10 to 100 cm. In general, a larger internal diameter (e.g. 50 microns) corresponds to a larger length (e.g. 100 cm), while a smaller internal diameter (e.g. 10 microns) corresponds to shorter lengths (e.g. 10 cm). This capillary form of restrictor avoids the precipitation problems associated with crimping or other constrictions. A major advantage of the replaceable wafer is that the length of restrictor conduit 52 can be readily adjusted without changing the spacial relationship between the SFE cell 40 and heating block 56, by using of a wafer with the desired length of coiled conduit.

An important aspect of the invention is to maintain the restrictor at an elevated isothermal temperature (e.g 150° C.) during the extraction. Similarly, the SFE cell itself is also heated. As illustrated, the heating means for SFE cell 40 is preferably in the form of a containment cell or oven 68 which surrounds cell 40. Oven 68 can be heated directly (e.g. direct current) or indirectly (e.g. exposure to a heat source such as a heating block, oven, thermal, tape, heated fluid or other source). The heating block has separate temperature controls.

The collection system of the present invention includes decompression chamber means in open communication with liquid solvent chamber means. The exit port from the flow restrictor conduit 52 projects into the decompression chamber means and preferably is free of liquid solvent contact.

Figure 6:
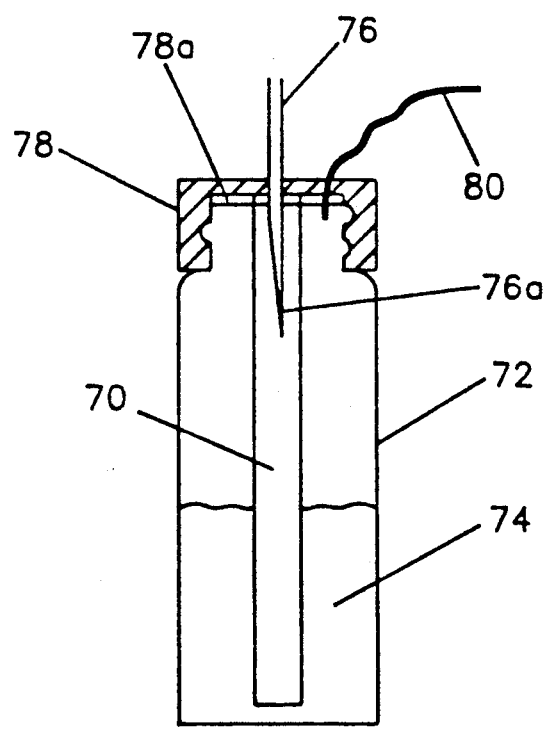
FIGS. 6 and 7 are two different forms of collection systems according to the invention.

In the embodiment of FIG. 6, decompression chamber means is in the form of an inner tube 70 disposed in a receptacle or vial 72 containing liquid solvent 74. As illustrated, needle 76a of restrictor conduit 76 projects through the thin top wall or septum 78a of cap 78. Supercritical fluid expansion into tube 70, forces solvent to flow toward the bottom of the tube. The supercritical fluid exits the bottom the tube and bubbles upwardly through solvent 74. The supercritical fluid exits vent 80 in the form of decompressed gas.

Internal precipitation of solute is avoided by adequate heating of restrictor conduit 76. Since there in no direct solvent contact with conduit 76, the solvent may be cooled by cooling block 66 (illustrated in FIG. 2) to maximize solvent trapping by dissolution and prevent solvent loss by heated contact with the tube. For this purpose, cooling block 66 may be cooled by a flowing refrigerant such as an ethyleneglycol/water mixture. A preferred temperature for the solvent is on the order of 5° to 10° C.

In solvent chamber means, specifically vial 72, the solvent traps, typically by dissolution, low molecular weight compounds present in the supercritical fluid. Such low molecular weight compounds typically are organic compounds with carbon chains of about 5 to 13 inches in length. In contrast, high molecular weight compounds (typically organic compounds with carbon chain length of at least about 14) are trapped on the interior walls of the decompression chamber means, specifically tube 70, prior to reaching the solvent.

After withdrawal of restrictor 76, vial 72 may be readily removed and connected to suitable separation means, such as a chromatographic column and detector such as a 621-D SFC/GC chromatograph sold by Dionex. In this mode the system is referred to as an off-line system. It is noted that the system is applicable to an on-line system in which the restrictor conduit is connected to the inlet of the separation means, e.g. a chromatography column.

In another embodiment of the collection system, not shown, the restrictor conduit needle may penetrate the cap 78 in the annular region around inner tube 70 to drive the solvent into inner tube 70 under gas pressure within the annular space. In this instance, the high molecular weight compounds deposit on the inner walls of vial 72 and the outer wall of inner tube 70. Here, the low molecular compounds are trapped in remaining solvent, if any, in the annular space and in the solvent in inner tube 70. The low and high molecular weight compounds may then be recovered by conventional means.

Figure 7:
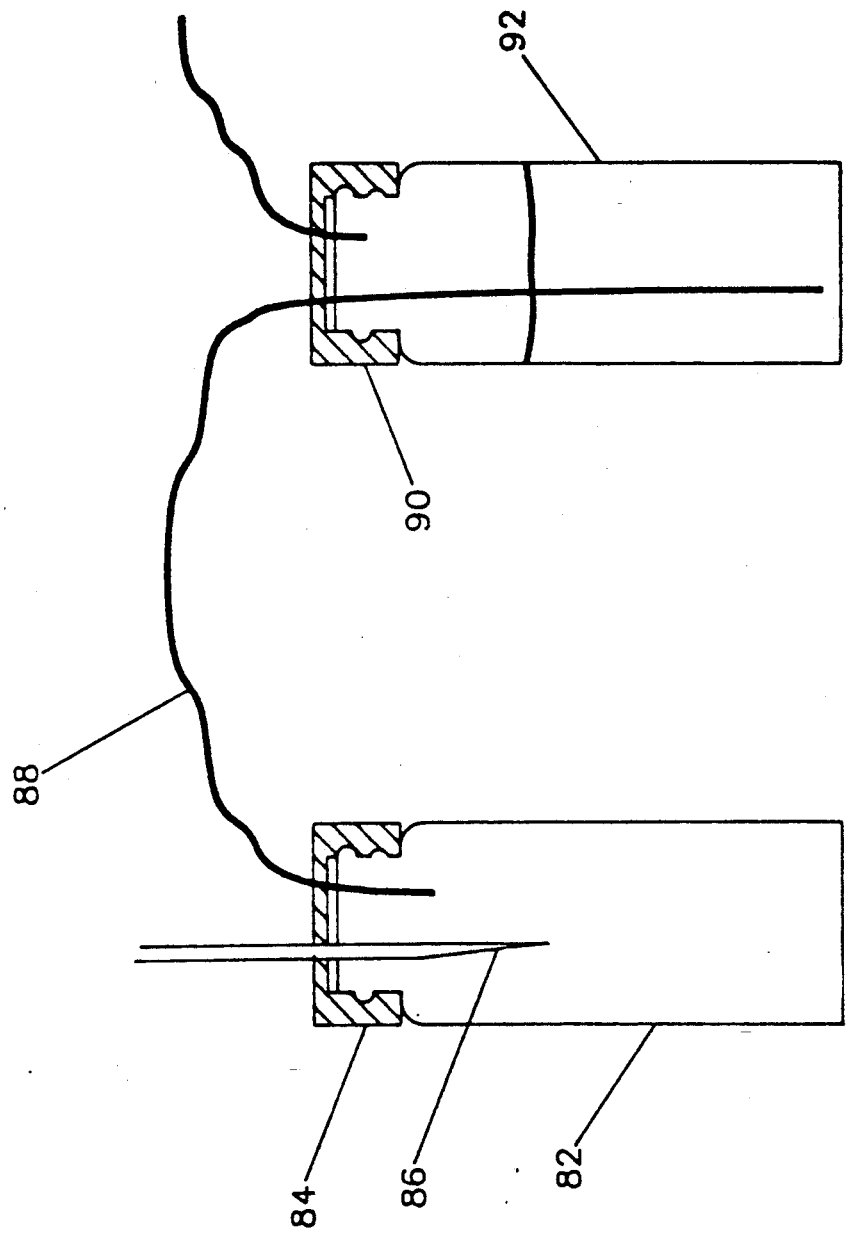

In another embodiment of the collection system (FIG. 7), two independent receptacles or vials are employed. Here, the decompression chamber means is in the form of vial 82 including stopper 84 through which restrictor 86 penetrates. A transfer tube 88 also penetrates stopper 84 and stopper 90 of liquid solvent chamber means defined by vial 92. Transfer tube 88 preferably is long enough to project towards the bottom of the solvent present in vial 92. In this manner, the high molecular compounds deposit on the walls of decompression chamber means within vial 82 while the low molecular weight compounds are trapped in solvent within vial 92. Both vials are suitably cooled as within a vial cooling block described above.

In operation of the foregoing system, the sample is first deposited in the sample cell in a conventional manner. Then, supercritical fluid is pumped through the sample cell at typical pressure of 4000 to 6000 psi and through capillary tube 52 to exit restrictor needle 52d which projects through the septum into the decompression zone which can be a tube within a vial, the first of a two vial system. In either event, the SFE sample cell is preheated to about 75° C., while the restrictor capillary conduit is preheated to about 100° C. This is typically accomplished by an oven within which the wide portion of the restrictor conduit is contained. Also, the oven heats the manifold 14, tubing sample cell 20 and restrictor conduit portion 52a. The heating block 56 within which the wafer containing the coiled portion of the restrictor is retained is independently heated by a separate heating block.

The high molecular weight compounds are deposited on the walls of the decompression chamber. The pressure from the SFE cell drops from extraction pressure to atmospheric pressure in the decompression cell.

Preferably the end of the restrictor needle is not contained in solvent, and so the solvent is not heated by the needle.

After flow through the decompression chamber, the supercritical fluid containing solute compounds of low molecular weight flows into the liquid solvent (e.g. hexane) in which the low molecular weight compounds are trapped typically by dissolution. The solvent is retained at a low temperature, e.g. 5° to 10° C. for maximum collection and maintenance of the volume of volatile solvent.

Thereafter the supercritical fluid in the form of a low pressure gas which has been stripped of solute passes out the system.

To recover and detect the solutes of interest, the cooling block 66 is then lowered out of contact with the restrictor needle and is tilted 30° to provide access to the vials. The vials can then be removed.

The walls of the decompression zone (e.g., the vial walls) can be washed with the remaining collection solvent and directed to an appropriate analytical means such as a gas chromatograph to determine simultaneously both the heavy and light molecular weight compounds. Alternately, the walls of the decompression zone can be washed with fresh solvent, and then the remaining collection solvent and the solvent used to clean the decompression zone can be analyzed for the light and heavy molecular weight compounds, respectively, by separate procedures.

Figure 8:
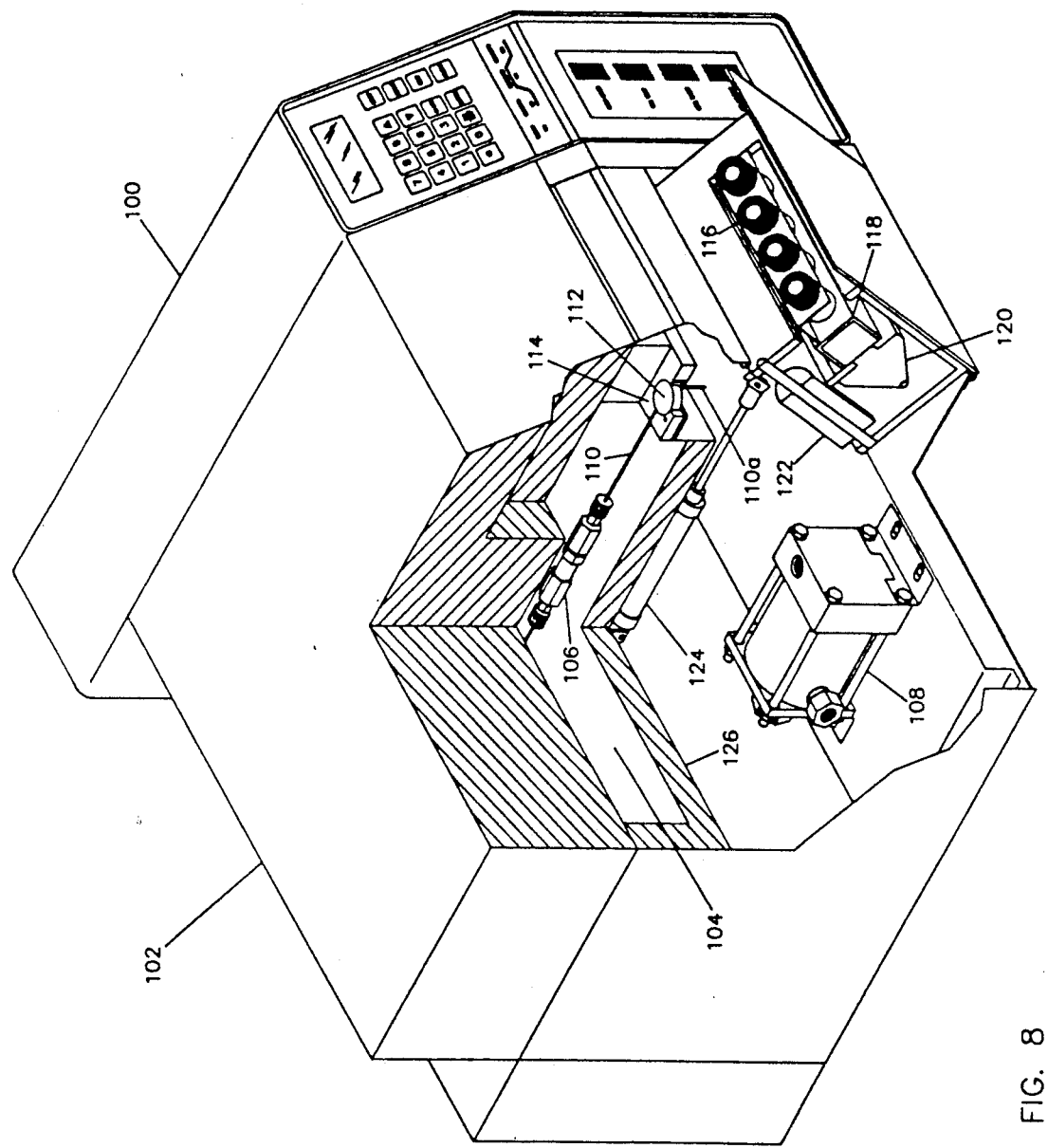
FIG. 8 is a perspective view, partially broken away, of the system of the present invention.

FIG. 8 illustrates a perspective view, partially broken away, of a complete off-line SFE/collection system incorporating the present invention. The system includes a housing 100 with an oven lid 102 which is connected by a back hinge and pivots between a closed position, as illustrated in FIG. 8, and an open position in which the interior of oven cavity 104 is exposed. Sample cell 106, a high pressure cell holding sample material to be extracted, is supplied with high pressure carbon dioxide pumped by reciprocating pump 108 connected to a manifold, not shown, connected in turn to each of the sample cells. As described above, the outlet of sample cell 106 is connected through restrictor conduit 110 which coils in disk 112 terminating in a needle 110a. Disk 112 is removably seated in a cylindrical well of heating block 114 below which needle 110a projects.

Collection vials 116 are retained in wells of cooling block 118 which is cooled by thermoelectric chips which area connected to heat sink 120. A vial lifting air cylinder 122 actuates up and down movement of cooling block 118 and cooling system 120 to cause the septums on vials 116 to be pierced by needles 110a and released after completion of collection. A door-opening cylinder 124 is connected between the main block of housing 126 and a corner of cooling block 118 serving to pivot block 118 from a vertical position to 30° from the vertical, as illustrated, to provide access to the vials for loading and unloading.

The following Example 1 is for the purpose of illustrating the present invention.

EXAMPLE 1

Two grams of sediment which was contaminated with polycyclic aromatic hydrocarbons (PAH) were weighed out into each of two extraction cells. Two cells were used to have replicate analyses of the same sample. The cells' dimensions are 5 cm × 9.4 mm i.d., and their material of construction is 316 stainless steel. The cell end caps contain metal frits with a pore size of 2 $\mu$m to retain the sediment sample in the cell during extraction. An SFE cell of this type is sold under the 6000 PSI Dionex model designation by Dionex Corporation. A portion (100 $\mu$L) of an internal standard solution containing five surrogate compounds (Nitrobenze-d5, 2-Fluorobiphenyl, Phenol-d5, 2-Fluoropohenol, and 2,4,6-Tribromophenol) each at a concentration of 5000 $\mu$g/mL was added to the sediment samples. The end caps of the cells were placed on the cells and tightened with a wrench to eliminate leaking during the extraction.

The inlet is connected to a manifold which can accommodate several cells simultaneously. This manifold is located in the temperature controlled region of the oven along with the cells and associated tubing. The manifold is also in communication with the pump via $\frac{1}{8}$" i.d. stainless steel tubing. A valve is placed between the pump and manifold to control the delivery of the extraction fluid to the manifold and extraction cells. The pump is a DSTV-122 15K PSI reciprocating pump sold by Haskel, Inc., Burbank, Calif.

The outlet end of each cell is connected to the inlet end of a coiled restrictor. The restrictors used in this example were 20 cm long and 30 $\mu$m i.d. The fused silica was held on the inside of the stainless steel tubing using a thermally conducting epoxy (such as H65-175MP from Epoxy Technologies, Billerica, Mass.).

The coiled portion of the stainless steel tubing was potted in a cylindrical wafer using the same epoxy. The end of the restrictors which is connected to the cell has appropriate high pressure fittings to make the connection. The other end has been sharpened to a needle point to pierce the septum lid of the vials and produce a leak-free seal.

The restrictors are placed in a metal block which is temperature controlled up to 200° C. by the use of a heater and thermocouple feedback. The use of the coiled design and the epoxy ensure uniform temperature throughout the entire length of the restrictors. In this example the restrictors were heated to 150° C. after they were connected to the extraction cells and held at a constant temperature for the entire extraction.

The oven is an insulated, forced-air heated chamber capable of temperature control from 40° C. to 150° C. For this example, the extraction temperature was 60° C.

A two-vial trapping arrangement was used. The dimensions of the borosilicate vials are approximately 7.5 cm high by 2.8 cm o.d. with a volume capacity of approximately 30 mL. The caps consist of standard screw-tops with Teflon-faced silicon septa. Five mL of hexane was used in one vial as the trapping solution. The first vial was empty, and the transfer tube between the two vials was $\frac{1}{8}$" o.d. teflon tubing (approximately 9 inches long). The vent line was a stainless steel syringe needle (18 gauge). The vials were held in a rack cooled to 5° C. by use of a cold circulating bath. (Alternately, the rack can be cooled by using thermoelectric chips which produce cooling when electrical current is supplied to them). The sharpened end of the restrictor is poked through the septum lid until it extends about an inch into the vial.

The pump was then pressurized to 400 atm for the extraction as the oven was heated to 75° C. and the restrictors to 150° C. When all the operating conditions had been achieved, the valve between the pump and the extractor was opened for 40 minutes, and the extraction proceeded. After the extraction period, the valve was closed, and the cells were allowed to depressurize for five minutes. The vials were then removed, the dry vial was washed with the solvent from the second vial, and this solution, after adjusting the volume to exactly 1.0 mL, was then analyzed by GC.

What is claimed is:

1. A collection apparatus for recovering chemical compounds carried in a high pressure effluent stream produced from supercritical fluid extraction means having an extraction exit end, said apparatus comprising:
   (a) decompression chamber means;
   (b) conduit means connected at one end thereof to the extraction exit end and including a conduit exit port at its other end disposed in said decompression chamber means, said conduit means including a flow restrictor capillary tube segment for maintaining fluid pressure upstream of said decompression chamber, said conduit means including a coiled segment located between the extraction exit end and the conduit exit port;
   (c) heating means, comprised of a heat conductive block having said coiled segment embedded therein, disposed adjacent said conduit means for heating at least a portion of said conduit means;
   (d) liquid solvent chamber means containing a quantity of liquid solvent therein and having a solvent chamber exit port, said liquid solvent chamber means being in open communication with said decompression chamber means, said open communication being such that the effluent, after passing through said decompression chamber means, passes through said quantity of liquid solvent in the liquid solvent chamber means, and wherein said conduit exit port is spaced apart from said quantity of liquid solvent.

2. The collection apparatus of claim 1 in which said decompression chamber means and said liquid solvent chamber means comprise first and second independent containers, respectively.

3. The collection apparatus of claim 1 in which,
said liquid solvent chamber means comprises a liquid solvent container for holding said quantity of liquid solvent,
and said decompression chamber means comprises a tube disposed within said liquid solvent container, said tube having a tube exit port defined by one end and a tube entrance port defined by an opposite end, said tube exit port providing said open communication between said decompression chamber means and said liquid solvent chamber means, said conduit exit port projecting through said tube entrance port into said tube.

4. The collection apparatus of claim 3 in which,
said tube exit port terminates in said quantity of liquid solvent.

5. The collection apparatus of claim 1 further including:
a septum hermetically disposed across an inlet port defined by said decompression chamber means; and
said conduit exit port is in a form capable of piercing and being positioned through said septum into said decompression chamber means.

6. The collection apparatus of claim 1 in which,
said coiled segment is of a predetermined length.

7. The collection apparatus of claim 1 in which,
said capillary tube segment is heated along a substantial portion by said heating means.

8. An extraction and collection apparatus comprising:
(a) supercritical fluid extraction means, having an extraction exit end, for extracting chemical compounds in a high pressure effluent stream; and
(b) collection means for recovering said chemical compounds carried in said effluent including
(1) decompression chamber means,
(2) conduit means communicably coupling said supercritical fluid extraction means to said decompression chamber means and terminating at a conduit exit port at said decompression chamber means, said conduit means including a flow restrictor capillary tube segment for maintaining fluid pressure upstream of said decompression chamber,
(3) heating means disposed adjacent said conduit means for heating at least a portion of said conduit means, and
(4) liquid solvent chamber means containing a quantity of liquid solvent therein to a level below said exit port of said conduit means disposed in said decompression chamber means such that said conduit means is free of contact with said liquid solvent during passage of effluent therethrough, said liquid solvent chamber means having a solvent chamber exit port and being in open communication with said decompression chamber means, said open communication being such that the effluent, after passing through said decompression chamber means, passes through said quantity of liquid solvent in the liquid solvent chamber means.

9. A collection apparatus for recovering chemical compounds carried in a high pressure effluent stream produced from supercritical fluid extraction means having an extraction exit end, said apparatus comprising:
(a) liquid solvent chamber means containing a quantity of liquid solvent therein;
(b) decompression chamber means including a structure defining an interior chamber airspace and having a chamber exit port therefrom terminating in said liquid solvent;
(c) conduit means connected at one end thereof to the extraction exit end and including a conduit exit port at its other end disposed in said interior chamber airspace of said decompression chamber means and positioned to be substantially free of contact with said liquid solvent, said conduit means including a flow restrictor capillary tube segment for maintaining fluid pressure upstream of said decompression chamber; and
(d) heating means disposed adjacent said conduit means for heating at least a portion of said conduit means;
wherein, said liquid solvent chamber means is in open communication with said decompression chamber means such that the effluent, after passing through the airspace of said decompression chamber means, passes through said quantity of liquid solvent in said liquid solvent chamber means.

10. The collection apparatus of claim 9 in which,
said heating means is comprised of a heat conductive block, and
said conductive means includes a coiled segment located between the exit end of said extraction means and the exit port of said conduit means, wherein said coiled segment is embedded in said heat conductive block.

11. The collection apparatus of claim 9 in which,
said decompression chamber means and said liquid solvent chamber means comprise first and second independent containers, respectively.

12. The collection apparatus of claim 9 in which,
said liquid container solvent chamber means comprises a liquid solvent container for holding said quantity of liquid solvent,
and said decompression chamber means comprises a tube disposed within said liquid solvent container, said tube having a tube exit port defined by one end and a tube entrance port defined by an opposite end, said tube exit port providing said open communication between said decompression chamber means and said liquid solvent chamber means, said conduit exit port projecting through said tube entrance port into said tube.

13. The collection apparatus of claim 9 further including:
a septum hermetically disposed across an inlet port defined by said decompression chamber means; and
said conduit exit port is in a form capable of piercing and being positioned through said septum into said decompression chamber means.

14. A collection apparatus for recovering chemical compounds carried in a high pressure effluent stream produced from supercritical fluid extraction means having an extraction exit end, said apparatus comprising:

(a) a first independent container including decompression chamber means;
(b) conduit means connected at one end thereof to the extraction exit end and including a conduit exit port at its other end disposed in said decomposition chamber means, said conduit means including a flow restrictor capillary tube segment for maintaining fluid pressure upstream of said decompression chamber means;
(c) heating means disposed adjacent said conduit means for heating at least a portion of said conduit means;
(d) a second independent container including liquid solvent chamber means containing a quantity of liquid solvent and a solvent chamber exit port, said liquid solvent chamber means being in open communication with said decompression chamber means by a transfer tube connecting said first independent container to said second independent container, said open communication being such that the effluent, after passing through said decompression chamber means, passes through said transfer tube and said quantity of liquid solvent in the liquid solvent chamber means.

* * * * *